(12) United States Patent
Kwok et al.

(10) Patent No.: US 7,958,892 B2
(45) Date of Patent: Jun. 14, 2011

(54) AIR DELIVERY SYSTEM

(75) Inventors: Philip Rodney Kwok, Chatswood (AU);
Muditha Pradeep Dantanarayana,
Cherrybrook (AU); Mark Bertinetti,
Ermington (AU)

(73) Assignee: ResMed Limited, Bella Vista (AU)

( * ) Notice: Subject to any disclaimer, the term of this patent is extended or adjusted under 35 U.S.C. 154(b) by 1251 days.

(21) Appl. No.: 11/494,522

(22) Filed: Jul. 28, 2006

(65) Prior Publication Data

US 2007/0023045 A1 Feb. 1, 2007

Related U.S. Application Data

(60) Provisional application No. 60/703,457, filed on Jul. 29, 2005.

(51) Int. Cl.
*A61M 11/00* (2006.01)
(52) U.S. Cl. .......... 128/204.18; 128/204.21; 128/204.23
(58) Field of Classification Search ............. 128/200.24, 128/203.11, 204.18, 204.21, 204.23, 205.24
See application file for complete search history.

(56) References Cited

U.S. PATENT DOCUMENTS

| 6,705,315 | B2 | 3/2004 | Sullivan et al. |
| 7,188,621 | B2 * | 3/2007 | DeVries et al. .......... 128/204.21 |
| 2003/0066529 | A1 | 4/2003 | Truschel et al. |
| 2007/0287895 | A1 * | 12/2007 | Brown .......................... 600/301 |

FOREIGN PATENT DOCUMENTS

| WO | WO 02/02169 | 1/2002 |
| WO | WO 02/18002 | 3/2002 |
| WO | WO 03/024335 | 3/2003 |
| WO | WO 2005/028009 | 3/2005 |
| WO | WO 2005/099798 | 10/2005 |

OTHER PUBLICATIONS

U.S. Appl. No. 60/505,718, filed Sep. 2003, Kwok.

* cited by examiner

*Primary Examiner* — Steven O Douglas
(74) *Attorney, Agent, or Firm* — Nixon & Vanderhye P.C.

(57) ABSTRACT

An air delivery system includes a controllable flow generator, a primary controller, and an auxiliary controller. The flow generator is operable to generate a supply of pressurized breathable gas to be provided to a patient for treatment. The primary controller is associated with at least one primary control feature to select at least a first aspect of operation of the flow generator. The auxiliary controller is associated with at least one auxiliary control feature to select at least a second aspect of operation of the flow generator. The second aspect selected by the auxiliary controller is different than the first aspect selected by the primary controller. The primary and auxiliary controllers may be interchangeably usable to control operation of the flow generator.

47 Claims, 5 Drawing Sheets

AIR DELIVERY SYSTEM

CROSS REFERENCE TO RELATED APPLICATION

This application claims the benefit of U.S. Provisional Application No. 60/703,457, filed Jul. 29, 2005, which is incorporated herein by reference in its entirety.

FIELD OF THE INVENTION

The present invention relates to a flow generator used in the treatment, e.g., of Sleep Disordered Breathing (SDB) with CPAP or Non-Invasive Positive Pressure Ventilation (NIPPV).

BACKGROUND OF THE INVENTION

A flow generator typically includes a housing with an integrated control panel for controlling the delivery of pressurized air to be provided to a patient for treatment. Treatment may be provided in various forms, from both simple CPAP systems to more complex non-invasive positive pressure ventilation (NIPPV), such as a Bi-level pressurized gas delivery system. The flow generator may be structured to administer only one form of treatment, or the flow generator may be structured to administer various forms of treatment.

Regardless of the type of flow generator, the control panel of the flow generator allows a clinician and/or patient to adjust the operating parameters or settings of the flow generator for a particular treatment. When the treatment is more complex, the control panel may be relatively advanced with multiple menus and features. If the operating parameters for a treatment are not appropriately selected, e.g., selected by an untrained patient, the treatment may be ineffective and/or harmful to the patient, or the patient simply will not use the apparatus.

Known control panels provide security codes to prevent the patient from inappropriately adjusting certain operating parameters. However, if the patient learns the security codes and/or the security codes are not implemented, the patient can access the same operating parameters as a trained clinician. Therefore, a need has developed in the art to provide improvements to known flow generators to prevent inappropriate selection of operating parameters.

SUMMARY OF THE INVENTION

One aspect of the invention is directed towards an air delivery system including a flow generator with interchangeable controllers to control operation of the flow generator, wherein one of the controllers includes basic features for use by a patient and the other of the controllers includes more advanced features for use by a trained clinician.

Another aspect of the invention relates to an air delivery system including a controllable flow generator, a primary controller, and an auxiliary controller. The flow generator is operable to generate a supply of pressurized breathable gas to be provided to a patient for treatment. The primary controller is associated with at least one primary control feature to select at least a first aspect of operation of the flow generator. The auxiliary controller is associated with at least one auxiliary control feature to select at least a second aspect of operation of the flow generator. The second aspect selected by the auxiliary controller is different than the first aspect selected by the primary controller. The primary and auxiliary controllers may be interchangeably usable to control operation of the flow generator.

Yet another aspect of the invention relates to an air delivery system including a controllable flow generator and a primary controller. The flow generator is operable to generate a supply of pressurized breathable gas to be provided to a patient for treatment. The primary controller is detachably mountable to the flow generator. The controller is associated with at least one primary control feature to select or control at least a first aspect of operation of the flow generator.

Yet another aspect of the invention relates to an air delivery system including a flow generator and a primary controller. The flow generator is structured to generate a supply of pressurized breathable gas. The flow generator is programmed with basic flow generator control features and advanced flow generator control features. The primary controller is only in communication with at least one of the basic control features of the flow generator.

Yet another aspect of the invention relates to an air delivery system including a flow generator and a blood glucose monitor. The flow generator is operable to generate a supply of pressurized breathable gas to be provided to a patient for treatment. The blood glucose monitor is detachably mountable to the flow generator.

Yet another aspect of the invention relates to an air delivery system including a controllable flow generator operable to generate a supply of pressurized breathable gas to be provided to a patient for treatment. The flow generator is operable in a continuous pressure delivery mode and a variable pressure delivery mode. At least one controller is configured to operate the flow generator in one of the continuous pressure delivery mode or the variable pressure delivery mode.

Other aspects, features, and advantages of this invention will become apparent from the following detailed description when taken in conjunction with the accompanying drawings, which are a part of this disclosure and which illustrate, by way of example, principles of the invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

Figure 1:
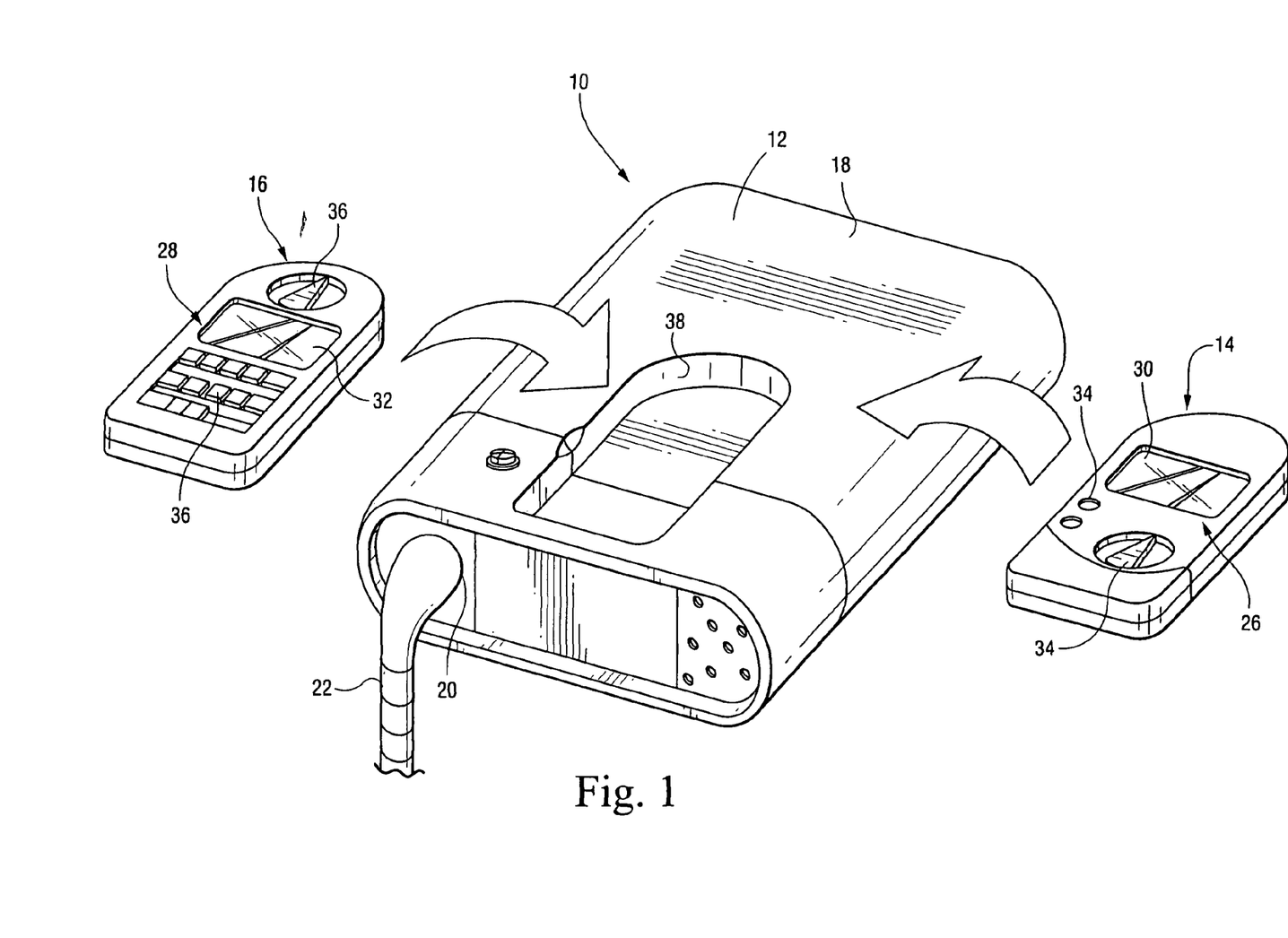
FIG. 1 is a perspective view of an air delivery system constructed according to an embodiment of the present invention, the air delivery system including a flow generator and interchangeable controllers.

FIG. 1 illustrates an air delivery system 10 constructed according to an embodiment of the present invention. The air delivery system 10 includes a controllable flow generator 12 operable to generate a supply of pressurized breathable air to be provided to a patient for treatment, e.g., of Sleep Disordered Breathing (SDB) with CPAP or Non-Invasive Positive Pressure Ventilation (NIPPV).

The air delivery system 10 provides interchangeable controllers 14 and 16 to control operation of the flow generator 12. One controller 14 includes basic features for use by the patient, and the other controller 16 includes more advanced features for use by a trained clinician. This arrangement prevents the patient from selecting inappropriate operating parameters of the flow generator 12, as discussed in greater detail below.

Flow Generator

As shown in FIG. 1, the flow generator 12 includes a housing 18 that supports a blower. As is known in the art, the blower is operable to draw a supply of air into the housing through one or more intake openings and provide a pressurized flow of air at an outlet 20.

Figure 2:
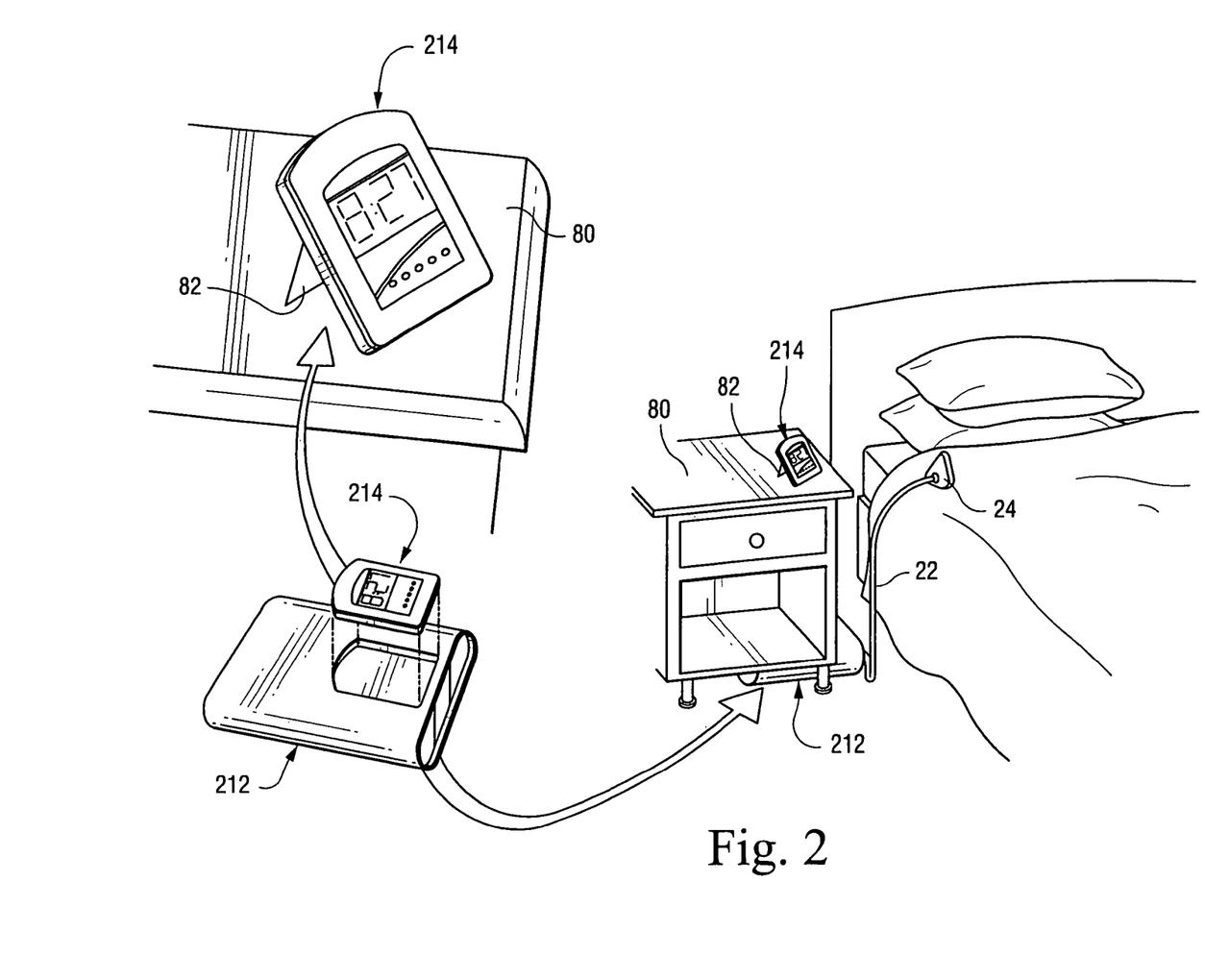
FIG. 2 is a perspective view of an air delivery system constructed according to another embodiment of the present invention.

The supply of pressurized air is delivered to the patient via an air delivery conduit 22 that includes one end coupled to the outlet 20 of the flow generator 12 and an opposite end coupled to a patient interface 24 (e.g., see FIG. 2).

The patient interface 24 comfortably engages the patient's face and provides a seal. The patient interface 24 may have any suitable configuration as is known in the art, e.g., full-face mask, nasal mask, oro-nasal mask, mouth mask, nasal prongs, etc. Also, any suitable headgear arrangement may be utilized to comfortably support the patient interface in a desired position on the patient's face.

Interchangeable Primary and Auxiliary Controllers

As noted above, the flow generator 12 is controllable by interchangeable controllers 14 and 16. Both controllers 14 and 16 are compatible with the flow generator 12 and may be interchangeably useable to control operation of the flow generator 12.

Also, a removable or interchangeable controller allows the controller to be installed into a replacement flow generator without having to reprogram as patient information may be stored in the removable controller.

As shown in FIG. 1, each of the controllers 14 and 16 is in the form of a hand-held device that may be wirelessly communicated with the flow generator 12. A suitable protocol controls whether the controller 14 or controller 16 operates to select operational aspects of the flow generator. For example, a "registration" button may be provided on the flow generator 12 that is configured to learn the operating frequency of a controller, e.g., radio frequency wireless technology.

Each controller 14 and 16 is operable to receive input, e.g., input signals, and to control operation of the flow generator 12 based on input signals. The controllers 14, 16 include a control panel 26, 28 that provides a display screen 30, 32 and one or more control features 34, 36, e.g., rotatable knob and buttons, respectively, that provide input signals. The control features 34, 36 of each controller 14, 16 may be manually selected to adjust operating parameters of the flow generator 12. As illustrated, the housing 18 of the flow generator 12 provides a recess 38, e.g., in the top wall, adapted to removably hold a selected one of the controllers 14, 16.

In the illustrated embodiment, one controller 14 is a primary controller that is operable to receive input signals from primary control features 34 to control operation of the flow generator 12. That is, the primary controller 14 includes relatively basic control features 34 adapted to control relatively basic aspects of the flow generator 12. The primary controller 14 is adapted for use by one who is relatively untrained, e.g., patient, to prevent the control of advanced aspects of the flow generator 12 that could alter the effectiveness of the treatment and/or cause harm to the patient. Also, the problem of patients being able to learn how to enter a program mode is ameliorated over current devices.

The other controller 16 is an auxiliary controller that is operable to receive input signals from auxiliary control features 36 to control operation of the flow generator 12. That is, the auxiliary controller 16 includes relatively advanced control features 36 adapted to control relatively advanced aspects of the flow generator 12. The auxiliary controller 16 may also include basic control features similar to those provided by the primary controller 14. In the illustrated embodiment, the auxiliary controller 16 provides more control features than the primary controller 14. Regardless, the auxiliary controller 16 provides control features that are different than the basic features provided by the primary controller 14, thereby allowing control of aspects not accessible by the primary controller 14. The auxiliary controller 16 is adapted for use by one, e.g., clinician, who is relatively trained in breathing treatment to allow control of advanced aspects of the flow generator 12 in order to tailor and/or adjust treatment provided to the patient. Furthermore, a service technician may have a controller version that allows the service technician to diagnose motor and/or circuit board operations, perform testing, and/or service the flow generator.

Thus, the flow generator 12 provides separate clinical and patient use. In an embodiment, the primary controller 14 is usable by a patient to operate the flow generator 12 in a manner that has been already pre-programmed by a trained clinician. This facilitates operation, and prevents the patient from changing the operating parameters.

The trained clinician pre-programs the flow generator 12 with the auxiliary controller 16. As noted above, the auxiliary controller 16 allows access to advanced features, e.g., via clinical menus, to program the flow generator 12 for a particular treatment. The auxiliary controller 16 may allow access to a memory that stores preferred operating parameters for a variety of treatments. The auxiliary controller 16 can then control the flow generator 12 based on the stored operating parameters in the memory for the selected treatment. Alternatively, the operating parameters for a selected treatment may be entered manually through the auxiliary controller 16. Further, the auxiliary controller 16 may allow access to a log of the patient's use for tracking purposes. This separate clinical/patient arrangement of the system allows the clinician to monitor operation and adjust operating parameters of the flow generator 12 without patient interference.

In an embodiment, the relatively basic controller 14 may be configured to control start, stop, and delay timer operations. When the flow generator 12 is registered with the relatively advanced controller 16, the relatively basic controller 14 still functions but the relatively advanced controller 16 can override the relatively basic controller 14. The relatively advanced controller 16 may also have patient setup and diagnostic functions such as adjusting pressure, checking patient compliance, and/or usage data. The relatively advanced controller 16 may be deregistered from the flow generator 12 once the flow generator 12 has been operated with the relatively basic controller 14 for more than one sleep session.

It is noted that a flow generator 12 may be controllable by a single controller or multiple controllers, with each of controllers having control features suitable for a particular treatment. For example, one controller may be usable to operate the flow generator as a simple CPAP device, one controller may be usable to operate the flow generator as a more advanced VPAP device, etc. Thus, the flow generator may be upgraded by communicating a new controller with the flow generator 12.

"Plug and Play" Arrangement

The air delivery system may provide a "plug and play" arrangement wherein the patient can simply communicate a controller with the flow generator 12 to automatically configure the flow generator 12 for a particular treatment. For example, the system may include controller to operate the flow generator as a CPAP device, and a controller to operate the flow generator as a VPAP device. Each controller would have a unique identifying feature so that the flow generator 12 can recognize which controller is communicated to the flow generator 12. Moreover, the controller can optimize operation of the flow generator 12 for the specified treatment.

Controller with Clock/Alarm

As noted above, the controller 14, 16 for the flow generator 12 may be wirelessly communicated with the flow generator 12. This arrangement allows the patient and/or clinician to easily adjust operating parameters of the flow generator 12 without being adjacent to the flow generator 12. Moreover, this arrangement allows the flow generator 12 and the controller 14, 16 to be in placed in separate locations.

For example, FIG. 2 illustrates an embodiment wherein the controller 214 is placed on a bedside table 80 and the flow generator 212 is placed under the table 80 away from the controller 214. As illustrated, the controller 214 includes a stand 82 structured to maintain it in a generally upright position on the table 80. Additionally, the controller 214 is structured to function as a clock with an alarm and/or radio. In use, the flow generator 212 can operate under the table 80 where it is concealed and the noise during use is less disturbing to the patient. Meanwhile, the patient can wirelessly control the flow generator 212 by the controller 214 which doubles as an clock, alarm, and/or radio.

Controller with Integral Blood Glucose Monitor

Figure 3:
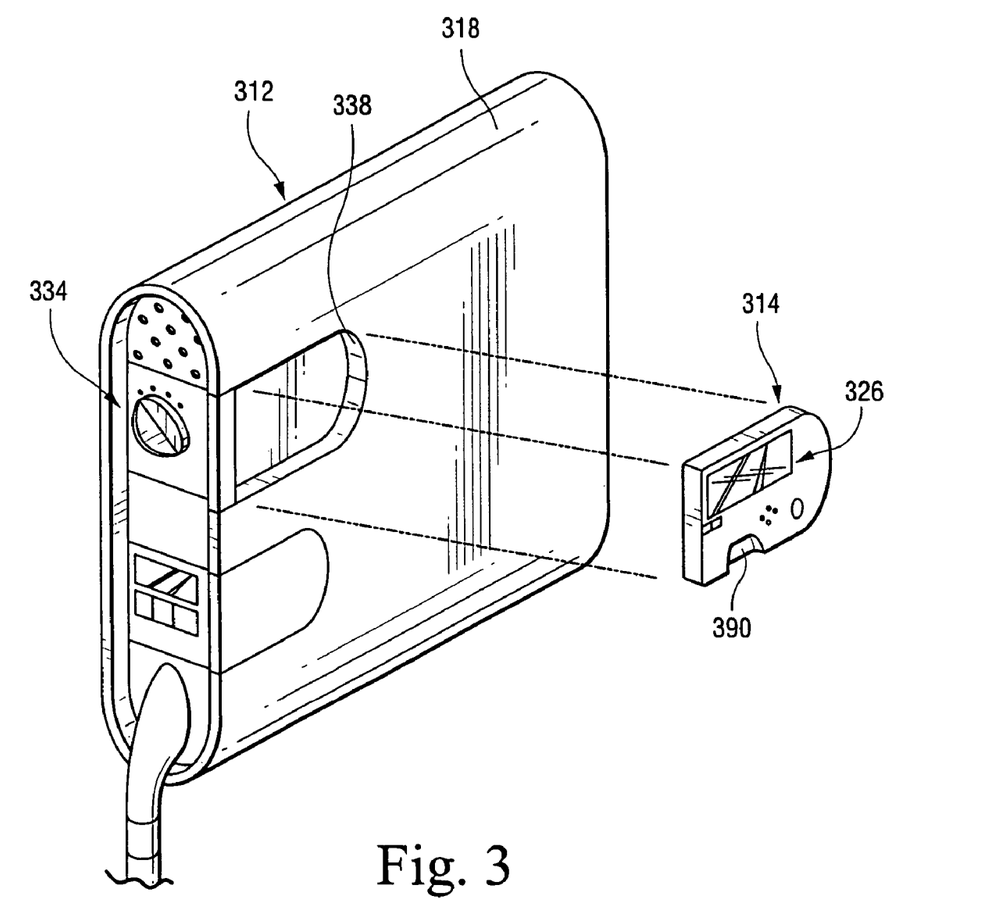
FIG. 3 is a perspective view of an air delivery system constructed according to still another embodiment of the present invention.

FIG. 3 illustrates an arrangement that includes a flow generator 312 and a removably attachable blood glucose monitor 314. The monitor 314 may be stored within a recess 338 provided in the housing 318 of the flow generator 312. As illustrated, the monitor 314 includes a control panel 326 and a recess 390 adapted to receive one of the patient's fingers for performing a blood glucose test. Information from the monitor 314 may be communicated to a physician via the flow generator. In an embodiment, the monitor 314 may adapt therapeutic pressure to optimize patient ventilation according to blood glucose levels.

In the illustrated embodiment, control features 334 for operating the flow generator 312 are provided on the housing 318. However, the control features 334 may be incorporated into the monitor 314 in a manner as described above.

Medicine Delivery Module

In another embodiment, the flow generator may include an add-on or integral medicine delivery module that delivers medicinal drug (e.g., insulin) into the air delivery path. The medicinal drug may include atomized, aerosol, and/or particulate medication, and the medicinal drug may be delivered into the air delivery path anywhere between the flow generator and the patient interface. In an embodiment, the medicine delivery module may be integrated with the controller and a bypass tube may add the drug into the air delivery path.

Input/Output to Couple Flow Generator and Controller

In illustrated embodiments, the controller 14, 214 for the flow generator 12, 212 may be wirelessly communicated with the flow generator 12, 212. However, the controller 14, 214 may be communicated with the flow generator 12, 212 in any other suitable manner.

Figure 4:
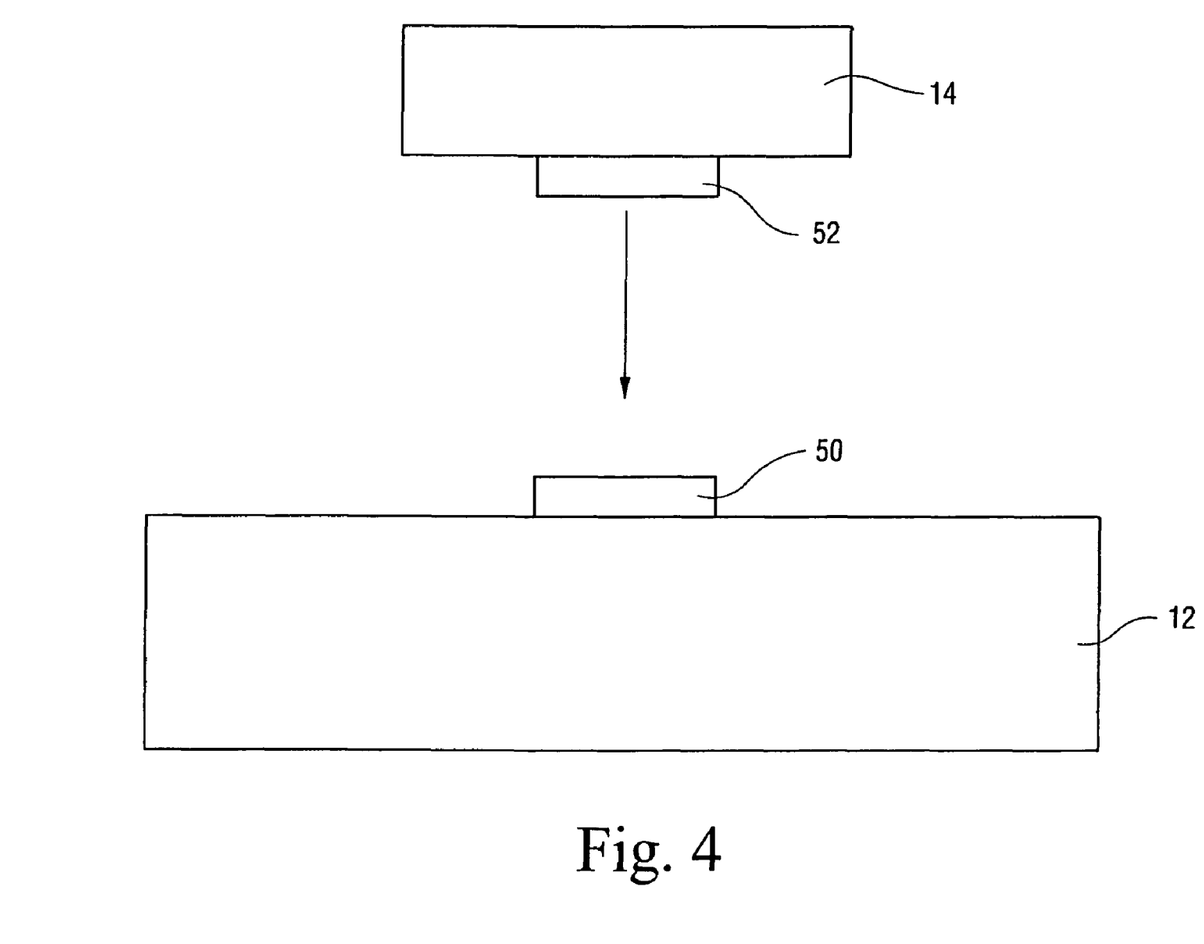
FIG. 4 is a schematic view of an air delivery system constructed according to yet another embodiment of the present invention.

For example, as schematically shown in FIG. 4, the flow generator 12 may include an input 50, and each controller 14 may include an output 52 (e.g., a communication port or an electrical contact) adapted to removably engage the input 50 to communicate each controller 14 with the flow generator 12. In an embodiment, the input may be provided within the recess 38 of the flow generator housing 18 shown in FIG. 1, and the output of the controller removably engages the input when the controller is removably inserted into the recess 38. The system may be disabled if a controller is not properly engaged with the flow generator. In another embodiment, the input and output are coupled via a cable.

Controller and Patient Monitors

The controller may be adapted to receive information from one or more patient monitors monitoring one or more patient parameters, e.g., patient's heart rate, breathing effort, etc. The patient and/or clinician may adjust the operating parameters of the flow generator based on the monitored parameters and/or the flow generator may automatically update the operating parameters based on the monitored parameters.

Programmable Controller

The controller may be programmable to operate other devices, e.g., television, stereo, etc. That is, the controller may be programmed via self learning to function as a remote control for the television, stereo, etc. and may interface with wireless smart wiring in the home to control lighting, etc.

Flow Generator with Single Controller

In an embodiment, the flow generator may be provided with a single removable controller that may be used by the patient and/or clinician. Thus, the controller may form a common unit that incorporates primary and auxiliary controllers. The common unit may be selectively attachable to and detachable from the flow generator in a manner as described above. Moreover, the auxiliary controller may only be accessible using an electronic key, e.g., only available at a health clinic, provided to only a licensed clinician or health provider.

In another embodiment, the single controller may be used by the clinician to program the flow generator, and the flow generator may be supplied to the patient without the controller so the patient cannot adjust the operating parameters.

In still another embodiment, the flow generator and the controller may be sold separately from one another. That is, the patient may purchase the controller separately from the flow generator depending on desired control features and/or treatment. Also, the patient could rent a flow generator when traveling, e.g., overseas, and therefore only travel with the controller which makes travel more convenient.

In yet another embodiment, the flow generator may be upgradable or simply changeable between AUTOSET® (generically known as auto-adjusting mode), CPAP, VPAP® (generically known as bi-level mode), etc, by using different controllers or a single controller that can select the desired operating mode. That is, the patient can upgrade a basic flow generator that is programmed and structured to operate in a plurality of modes (e.g., AUTOSET®, CPAP, VPAP®, etc., all available from ResMed) by using a new controller, and hence make the flow generator work like an AUTOSET®, CPAP, VPAP®, etc. The flow generator can be upgraded with a hardware upgrade, i.e., using a different controller, and/or a software upgrade, i.e., upgrading software of a single controller.

Controller Usable in Plurality of Flow Generators

In still another embodiment, the flow generator may include a single patient controller and a single technician controller. Moreover, the technician controller may be used in a plurality of flow generators. Thus, the technician may use a single controller to adjust the operating parameters of different flow generators.

Controller With Touchscreen Display

Figure 5A:
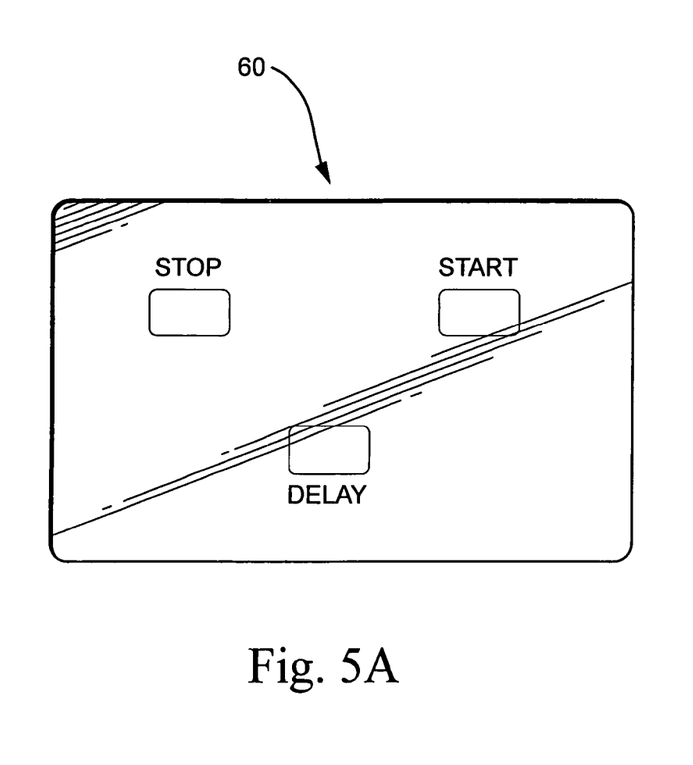
FIG. 5A is a plan view of a touchscreen display configured for a basic controller according to another embodiment of the present invention.
Figure 5B:
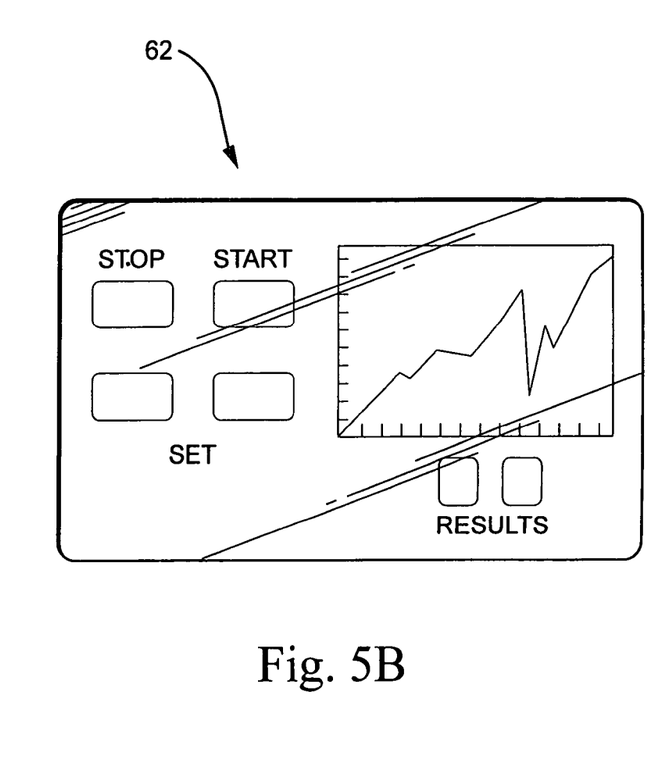
FIG. 5B is a plan view of a touchscreen display configured for an advanced controller according to another embodiment of the present invention.

In another embodiment, the controller may have a touchscreen display, which may be configured to display functions for operating certain types of flow generators and/or for certain user levels. The display may include a relatively large touchscreen with a configurable background that shows simple menus and information, and start/stop buttons. The clinician can set up the display to suit the user and/or the user can select which functions need to be displayed, i.e., buttons frequently used by the user. For example, FIG. 5A illustrates an embodiment of a touchscreen display 60 that is configured to include simple functions for a basic controller, and FIG. 5B illustrates an embodiment of a touchscreen display 62 that is configured to include more complex functions for a more advanced controller, e.g., clinician controller.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. An air delivery system, comprising:
    a controllable flow generator operable to generate a supply of pressurized breathable gas to be provided to a patient for treatment;
    a primary controller associated with at least one primary control feature to select at least a first aspect of operation of the flow generator; and
    an auxiliary controller associated with at least one auxiliary control feature to select at least a second aspect of operation of the flow generator, the second aspect selected by the auxiliary controller being different than the first aspect selected by the primary controller,
    wherein the primary and auxiliary controllers are interchangeably usable to control operation of the flow generator.

2. The air delivery system according to claim 1, wherein the primary and auxiliary controllers are separate and distinct structures from the flow generator and from one another.

3. The air delivery system according to claim 1, wherein the primary and auxiliary controllers are wirelessly communicated with the flow generator.

4. The air delivery system according to claim 1, wherein the flow generator includes a mounting portion adapted to alternatively support either the primary controller or the auxiliary controller.

5. The air delivery system according to claim 4, wherein the mounting portion includes an opening that generally matches the shape of each of the primary and auxiliary controllers.

6. The air delivery system according to claim 1, wherein the auxiliary controller includes more control features than the primary controller.

7. The air delivery system according to claim 1, wherein the auxiliary controller includes advanced control features accessible to a trained clinician.

8. The air delivery system according to claim 1, wherein at least one of the primary and auxiliary controllers includes a clock, an alarm, and/or a radio.

9. The air delivery system according to claim 1, wherein at least one of the primary and auxiliary controllers includes a stand structured to maintain the respective controller in a generally upright position on a support surface.

10. The air delivery system according to claim 1, wherein the primary controller and/or the auxiliary controller includes an integral blood glucose monitor.

11. The air delivery system according to claim 1, wherein the flow generator includes a registration feature that identifies an operating frequency of the primary controller and/or the auxiliary controller.

12. The air delivery system according to claim 1, wherein the flow generator, the primary controller and/or the auxiliary controller includes a medicine delivery module that delivers medicinal drug into a gas delivery path.

13. The air delivery system according to claim 1, wherein the primary controller and/or the auxiliary controller includes a configurable touchscreen display.

14. An air delivery system, comprising:
    a controllable flow generator operable to generate a supply of pressurized breathable gas to be provided to a patient for treatment; and
    a primary controller detachably mountable to the flow generator, the controller being associated with at least one primary control feature to select or control at least a first aspect of operation of the flow generator,
    wherein the primary controller is configured to select or control at least the first aspect of operation of the flow generator when the primary controller is detached from the flow generator.

15. The air delivery system according to claim 14, further comprising an auxiliary controller detachably mountable to the flow generator, the auxiliary controller being associated with at least one auxiliary control feature to select or control at least a second aspect of operation of the flow generator,
    wherein the first aspect is different than the second aspect.

16. The air delivery system according to claim 15, wherein the primary and auxiliary controllers are interchangeably and alternatively usable to control operation of the flow generator.

17. The air delivery system according to claim 15, wherein the primary and auxiliary controllers are wirelessly communicated with the flow generator.

18. The air delivery system according to claim 15, wherein the flow generator includes an opening adapted to support a respective one of the primary and auxiliary controllers.

19. The air delivery system according to claim 15, wherein the flow generator includes a registration feature that identifies an operating frequency of the primary controller and/or the auxiliary controller.

20. The air delivery system according to claim 15, wherein the flow generator, the primary controller and/or the auxiliary controller includes a medicine delivery module that delivers medicinal drug into a gas delivery path.

21. The air delivery system according to claim 15, wherein the primary controller and/or the auxiliary controller includes a configurable touchscreen display.

22. The air delivery system according to claim 14, wherein the primary controller includes an integral blood glucose monitor.

23. An air delivery system comprising:
- a flow generator structured to generate a supply of pressurized breathable gas, the flow generator being programmed with basic flow generator control features and advanced flow generator control features; and
- a primary controller only in communication with at least one of the basic control features of the flow generator,
- wherein the primary controller is detachably mountable to the flow generator and configured to control at least one of the basic control features of the flow generator when the primary controller is detached from the flow generator.

24. The air delivery system according to claim 23, further comprising an auxiliary controller in communication with the advanced control features and optionally in communication with the basic control features.

25. The air delivery system according to claim 24, wherein the primary and auxiliary controllers are separate units.

26. The air delivery system according to claim 24, wherein the primary and auxiliary controllers are alternatively mountable to the flow generator.

27. The air delivery system according to claim 24, wherein the flow generator includes a mounting recess having a shape matching that of the primary and auxiliary controllers.

28. The air delivery system according to claim 27, wherein a top surface of the primary and auxiliary controllers is substantially flush when seated in the mounting recess.

29. The air delivery system according to claim 24, wherein each of the primary and auxiliary controllers includes a wireless connection with the flow generator.

30. The air delivery system according to claim 24, wherein the primary controller includes a blood glucose monitor.

31. The air delivery system according to claim 30, wherein output from the blood glucose monitor is used as input to control the flow generator.

32. The air delivery system according to claim 24, wherein the primary and auxiliary controllers are formed on a common unit.

33. The air delivery system according to claim 32, wherein the common unit is selectively attachable to and detachable from the flow generator.

34. The air delivery system according to claim 24, wherein the auxiliary controller is accessible using an electronic key provided to only a licensed clinician or health provider.

35. The air delivery system according to claim 24, wherein the auxiliary controller is selectively usable with a plurality of different flow generators.

36. The air delivery system according to claim 24, wherein the flow generator includes a registration feature that identifies an operating frequency of the primary controller and/or the auxiliary controller.

37. The air delivery system according to claim 24, wherein the flow generator, the primary controller and/or the auxiliary controller includes a medicine delivery module that delivers medicinal drug into a gas delivery path.

38. The air delivery system according to claim 24, wherein the primary controller and/or the auxiliary controller includes a configurable touchscreen display.

39. An air delivery system, comprising:
- a flow generator operable to generate a supply of pressurized breathable gas to be provided to a patient for treatment; and
- a blood glucose monitor detachably mountable to the flow generator,
- wherein the blood glucose monitor includes a controller associated with at least one control feature to select or control operation of the flow generator.

40. An air delivery system. comprising:
- a flow generator operable to generate a supply of pressurized breathable gas to be provided to a patient for treatment; and
- a blood glucose monitor detachably mountable to the flow generator,
- wherein the flow generator includes an opening adapted to support the blood glucose monitor.

41. An air delivery system, comprising:
- a controllable flow generator operable to generate a supply of pressurized breathable gas to be provided to a patient for treatment, the flow generator being operable in a continuous pressure delivery mode and a variable pressure delivery mode; and
- at least a first controller configured to operate the flow generator in either the continuous pressure delivery mode or the variable pressure delivery mode.

42. The air delivery system according to claim 41, wherein the first controller is programmed in relation to the continuous pressure delivery mode and a second controller is programmed in relation to the variable pressure delivery mode.

43. The air delivery system according to claim 42, wherein the variable pressure delivery mode includes auto-adjusting mode.

44. The air delivery system according to claim 14, wherein the primary controller is configured to select or control at least the first aspect of operation of the flow generator when the primary controller is mounted to the flow generator.

45. The air delivery system according to claim 14, wherein the primary controller is in the form of a hand-held device.

46. The air delivery system according to claim 23, wherein the primary controller is configured to control at least one of the basic control features of the flow generator when the primary controller is mounted to the flow generator.

47. The air delivery system according to claim 23, wherein the primary controller is in the form of a hand-held device.

* * * * *